United States Patent [19]

McGuinness

[11] Patent Number: 5,088,482
[45] Date of Patent: Feb. 18, 1992

[54] CERVICAL BRACE

[76] Inventor: Charles McGuinness, 10 Karen Ave., Plainview, N.Y. 11803

[21] Appl. No.: 625,744

[22] Filed: Dec. 11, 1990

[51] Int. Cl.$^5$ .............................................. A61F 5/04
[52] U.S. Cl. ............................. 602/18; 128/DIG. 23; 602/32
[58] Field of Search ............... 128/75, 76 R, 78, 87 B, 128/DIG. 23

[56] References Cited

U.S. PATENT DOCUMENTS

| | | | |
|---|---|---|---|
| 2,820,455 | 1/1958 | Hall | 128/DIG. 23 |
| 3,776,224 | 12/1973 | McFarland | 128/75 |
| 3,779,549 | 12/1973 | MacNeil | 128/76 R |
| 4,383,523 | 5/1983 | Schurman | 128/75 |
| 4,735,196 | 4/1988 | Krag et al. | 128/75 |
| 4,793,334 | 12/1988 | McGuinness et al. | 128/87 B |
| 4,807,605 | 2/1989 | Mattingly | 128/75 |
| 4,854,306 | 8/1989 | Pujals, Jr. | 128/76 R |

FOREIGN PATENT DOCUMENTS 2233900 1/1991 United Kingdom .................. 128/75

*Primary Examiner*—Richard J. Apley
*Assistant Examiner*—Linda C. M. Dvorak
*Attorney, Agent, or Firm*—Collard, Roe & Galgano

[57] ABSTRACT

The invention provides a cervical brace with a torso engaging member, a chin support member and a head support member. The chin support member and head support member are adjustably mounted on the torso engaging member. The chin support member releases from the framework and pivots so as to allow simple mounting and removal without affecting the adjustments. The chin support member and head support member cooperatively restrict movement of the wearer's head.

23 Claims, 6 Drawing Sheets

CERVICAL BRACE

BACKGROUND OF THE INVENTION

The present invention relates to a cervical brace. In general, cervical braces are worn to correct or ease discomfort from spinal injuries, particularly spinal injuries in the area of the neck vertebrae. In particular, cervical braces are commonly used to rectify any spinal damage caused as a result of whiplash injury.

There are a number of types of such braces. For example, one type comprises a relatively stiff collar worn around the neck, which extends between the shoulders and the jawbone and chin of the wearer. While such collars do give a certain amount of support, they do not provide for adjustment to accommodate varying lengths of different people's necks. Thus, on some they may be relatively comfortable, while on others they can cause considerable discomfort. For example, in the case of an individual with a relatively short neck, such a collar may cause the chin to be retained at a totally incorrect angle. Further, for an individual with a relatively long neck, the chin may also be supported at the wrong angle. A further problem with such collars is that they are clearly visible for all to see, and, in general, are relatively unsightly. Furthermore, because they are worn completely around the neck, there is very little circulation of air between the collar and the neck. Accordingly, they tend to induce perspiration in the neck area which further leads to discomfort. Various attempts have been made to overcome the problems of such collars. Examples of such attempts are given in the following U.S. Patent specifications, namely, U.S. Pat. Nos. 3,724,452, 3,945,376, 4,383,523 and 4,628,913. In general, these cervical braces comprise a harness for mounting on the torso of the body, and a chin support member for supporting the chin of the wearer. The chin support member is mounted on a support bar which is adjustable upwardly and downwardly to accommodate wearers with different lengths of neck. However, while these devices partly overcome the problems of stiff collars in that at least the height at which the wearer's chin is supported can be adjusted, nonetheless, they do not provide for the different positions which individuals chins may take up, in other words, the position of a wearer's chin front to back. Accordingly, while the chin supports may be adjusted to accommodate different heights of chins, this does not ensure that the chin support will accurately or correctly engage the wearer's chin. For example, if a wearer has a chin which projects more than normally, or a wearer has a chin which projects less than normally, then the chin support will not adequately support the wearer's chin.

Another known device is the "halo" brace. Such a device also has a harness for mounting on the torso and upright members which extend to the top of the wearer's head. A "halo" or ring is attached to the upright members which encircles the head in the forehead area. Four equally-spaced adjusting screws are installed in the halo and screwed toward the wearer's head. Depressions are made in the skull to receive the adjusting screws. The screws are tightened so as to restrict movement of the head and neck. However, the device is not very effective and, in addition, is bulky and unsightly. Furthermore, problems can develop with a single skull depression requiring total refitting of the device.

An improved cervical brace is described in U.S. Pat. No. 4,793,334. This device overcame some of the problems with cervical braces, namely, the chin support member was adjustable both up and down, as well as front to back. However, the chin support member in this device was not comfortable as it "clamped" onto the wearer's chin. In addition, although a support is provided for the wearer's occiput, it is not sufficiently adjustable. Furthermore, the two-point support member for the chin support is not stable, i.e., it is flexible in the left-right direction. In addition, it has a complex harness assembly and requires changing the settings to remove the device.

There is, therefore, a need for a cervical brace which utilizes the advantages found in U.S. Pat. No. 4,793,334, and overcomes the deficiencies in the prior art. The present invention is directed toward providing such a cervical brace.

SUMMARY OF THE INVENTION

It is therefore an object of the present invention to provide a cervical brace which comprises a chin support member for supporting a wearer's chin which can be adjusted to engage a patient's chin accurately and snugly. In other words, it is a object of the invention to provide a cervical brace in which the chin support member is adjustable not only upwardly and downwardly but also forwardly and backwardly relative to the wearer.

It is also an object of the invention to provide a cervical brace which, as well as supporting the chin, also adjustably supports wearer's occiput, and thus the entire head. In other words, a cervical brace provided with a head support member that is adjustable upwardly, downwardly, forwardly and rearwardly.

A further object of the invention is to provide a cervical brace which can be relatively easily fitted and removed.

Another object of the invention is to provide a cervical brace in which the chin support member is removable.

Yet a further object is to provide a cervical brace with a plurality of adjustments that can easily be made by an individual with relatively little training with the device.

It is yet another object to provide a cervical brace which provides support by non-intrusive means, i.e., fits externally on the wearer.

These and other related objects are attained according to the invention by providing a cervical brace comprising a torso engaging member having a back portion and a front portion. The front portion in use being adjacent to the front of the torso and the rear portion, in use, being adjacent to the back of the torso. A chin support member is provided for engaging and supporting the chin of the wearer, mounting means for mounting the chin support member to the torso engaging member so that the chin support member is movable upwardly and downwardly in addition to backwardly and forwardly relative to the torso engaging member for accommodating, in use, different positions of a wearer's chin.

In one embodiment of the invention, the mounting means releasably mounts the chin support member to the torso engaging member.

Preferably, the mounting means comprises a strut extending at one end from the chin support member, and being pivotally connected at the other end to the front portion of the torso engaging member. The strut can suitably be fashioned as a turnbuckle.

Advantageously, a pair of brace members extends from the chin support member, and engages the front portion of the torso engaging member at a position spaced apart from the pivotal mounting of the strut, adjusting means being provided on the brace member for adjusting the length thereof. The adjusting means being suitably fashioned as adjusting nuts.

In a preferred embodiment of the invention, the brace member engages the front portion of the torso engaging member rearwardly of the strut.

Desirably, the strut and brace member form a three-point support for the chin support member.

Preferably, the torso engaging member comprises a tubular harness having a framework which comprises a pair of side members and a front, middle and rear member extending between the side members.

The chin support members can conveniently be disconnected at the brace member and pivoted away from the wearer's head secured by the strut. The can be done without affecting any of the adjustments thereon.

Advantageously, four head supporting uprights extend upwardly from the framework to, in use, extend adjacent the left side and right side of wearer's head, and the head supporting uprights are releasably engageable with the framework.

Such a configuration allows the wearer to easily put on and remove the cervical brace without altering any of its many adjustments. In this manner, the doctor can properly adjust the cervical brace and the wearer can remove the device any time without disturbing the settings. Also, the device can be equipped with simplified straps, only under the arms, for example, or no straps at all.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENTS

Figure 1:
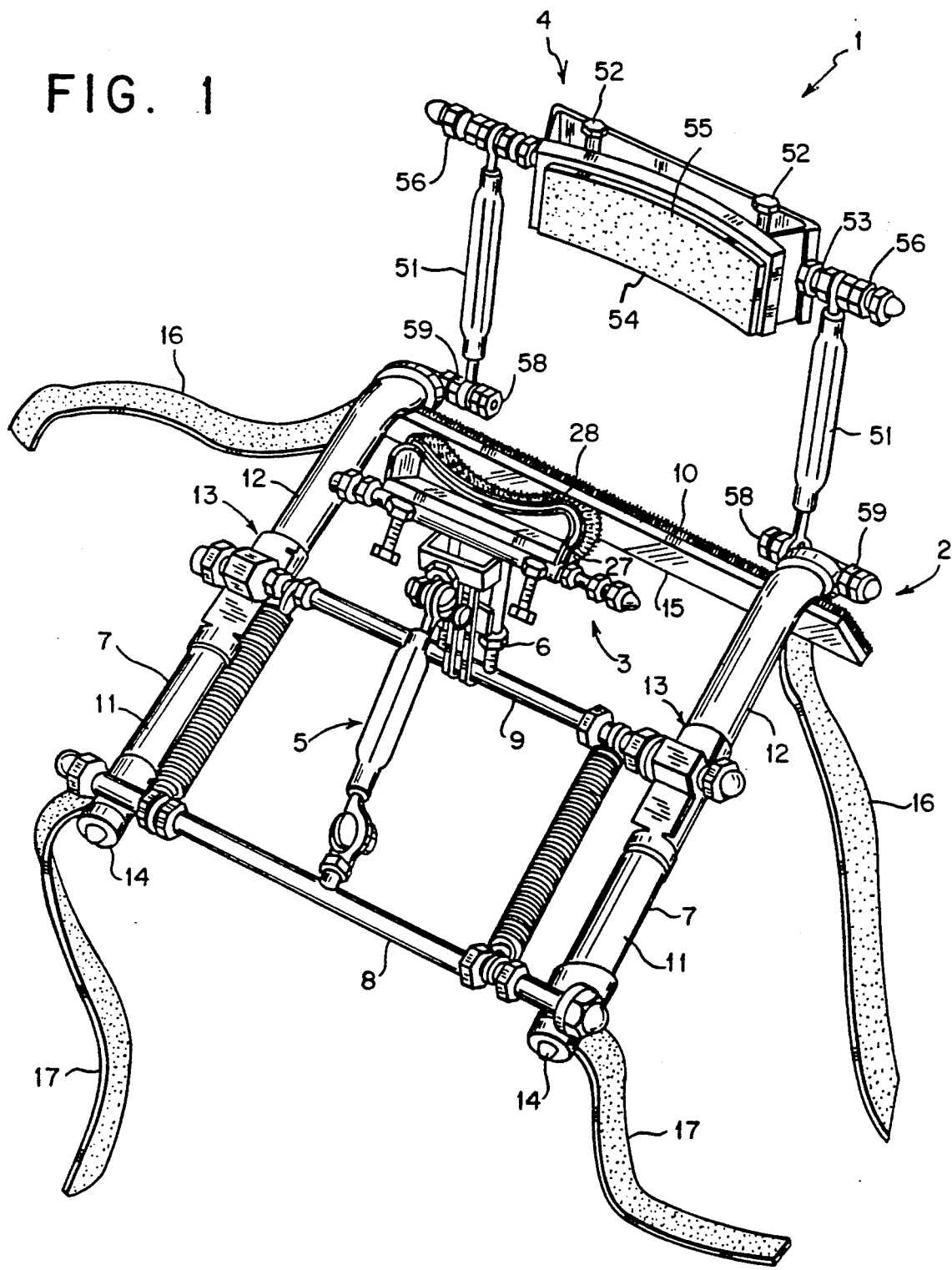
FIG. 1 is a perspective view of a cervical brace according to the invention.

Referring now to the drawings and, in particular to FIG. 1, there is provided a cervical brace according to the invention, indicated generally by the reference numeral 1. The cervical brace comprises a torso engaging member, which, in this case, is provided by a harness 2, which supports a chin support member 3 on mounting means and a rear head support member 4 on mounting means.

The mounting means for chin support member 3 comprises a strut 5, which extends from the chin support member 3 to harness 2. A brace member 6 also extends from chin support member 3 to harness 2. The strut 5 and brace member 6 are described in more detail below.

Harness 2 comprises a framework having a pair of side members 7 joined by a front member 8, a middle member 9, and a rear member 10, respectively. In this particular case, the side members 7 are a two-part assembly including a tubular metal section 11 and a tubular plastic section 12. Tubular metal section 11 supports front member 8 and middle member 9, while tubular plastic section 12 supports rear member 10. Tubular metal section 11 and tubular metal section 12 are adjustably joined generally in the area 13 (see FIG. 5).

A padded member 15 of soft, durable material is provided as rear member 10. (Padded member 15 can be attached, for example by Velcro ®, a hook and loop fastener, to allow changing of padded member 15.) Straps 16 and 17 extending from the front and rear members 8 & 10 secure the harness 2 around the upper torso of the wearer. Straps 16 and 17, e.g. extend under the armpits of the wearer and attach with Velcro ®. However, it has been found that the straps are not necessary to restrict movement of the head. Since the device operates like a wedge between the head and shoulders, it is secure without having to be strapped to the torso.

Chin support member 3 comprises an arcuate member 27 which is provided with a padded member 28. Padded member 28 can be attached, for example, by Velcro ®, to allow changing of padded member 28

Rear head support member 4 comprises a pair of upstanding members 51. A threaded cross-bar 53 extends between the upstanding members 51. An arcuate cross-member 54, which is provided with a padded surface 55, is mounted on threaded cross-bar 53 by adjusting means. Threaded cross bar 53 is secured to upstanding members 51 by a set of nuts 56 which correspond to threaded cross bar 53. Upstanding members 51 are attached to side members 7 by nuts 58 which correspond to bolts 59.

Figure 2:
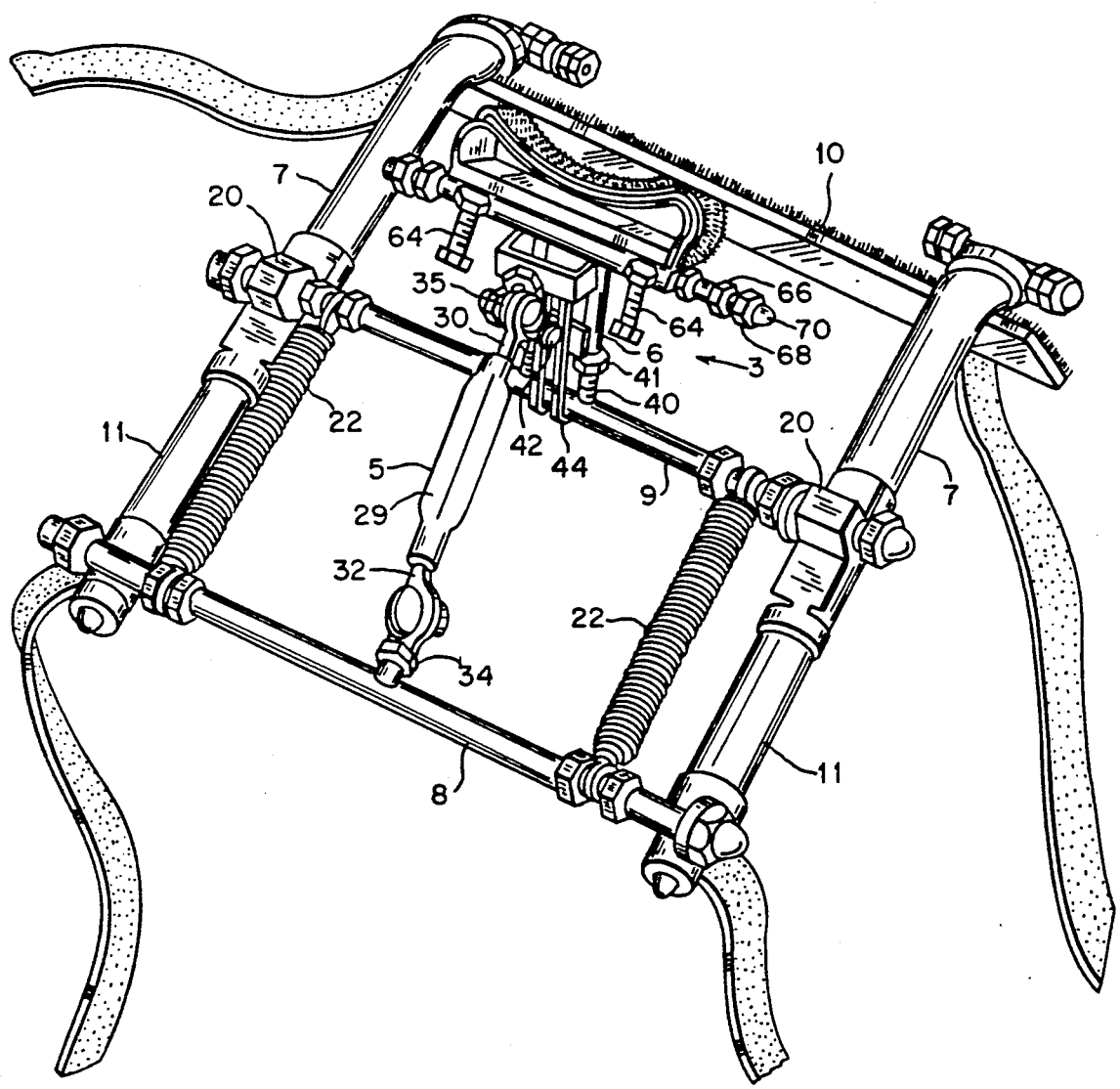
FIG. 2 is an enlarged perspective view of the chin support member.

FIG. 2 shows a more detailed view of chin support member 3 from FIG. 1. Each side member 7 has a clip 20 placed approximately centrally along side member 7, for example, on tubular metal section 11. Clip 20 extends outwardly from side member 7 and then bends parallel to side member 7. Clip 20, an L-shaped extension, forms a U-shaped receiving space in conjunction with side member 7. Middle member 9 sits within the receiving space formed by clip 20. It is held firmly in place by springs 22 which urge middle member 9 toward front member 8 due to springs 22 attachment to front member 8.

Strut 5 is shown as a turnbuckle. Cooperatively threaded to a central portion 29 of the turnbuckle are a first eyelet 30 and a second eyelet 32. First eyelet 32 is bolted to a front member eyelet 34 which is attached to front member 8. Second eyelet 32 is bolted to a chin support eyelet 35 which is attached to brace member 6. Eyelets 30 and 32 are screwed into oppositely threaded ends of central portion 29. The turnbuckle is shown substantially in its fully collapsed position. Central portion 29 can be rotated, for example, clockwise, so that both eyelets 30 and 32 become unscrewed due to eyelets 30 and 32 firm attachment. Such a rotation results in the extension of strut 5 in a direction 36. This generally pushes chin support member 3 backwardly towards the wearer. From an extended position central portion 29 can be rotated in an opposite direction, for example, counter-clockwise, resulting in a collapse of strut 5. This generally pulls chin support member 3 forwardly away from the wearer.

The forward and backward movement of chin support member 3 is translated to rotational movement of middle member 9 due to attachment by brace member 6. Since middle member 9 sits within a receiving space formed by clips 20, it is free to rotate. Springs 22 do not hinder free rotation as their ends are not fixably attached to middle member 9.

Brace member 6 has a pair of openings on its bottom end which receive a pair of brace bolts 40 which are fixably attached to middle member 9. These openings are of a larger diameter than the bolts and permit relatively free movement of brace member 6 with respect to brace bolts 40. Cooperatively threaded on brace bolts 40 are adjusting nuts 41. Adjusting nuts 41 screw along brace bolts 40 thus raising or lowering brace member 6. This generally pushes or releases brace member 6 upwardly or downwardly. The maximum downward position is defined by adjusting nuts 41 reaching middle member 9. The maximum upward position is defined by a guide screw 42, which is attached to brace member 6, reaching the end of a guide 44, as shown in FIG. 3.

It is possible to push middle member 9 toward rear member 10, against the biasing of springs 22, an amount sufficient for middle member 9 to clear clips 20. As can be seen in FIG. 3, such an action would allow chin support member 3 to swing away from the wearer in an arc 46. Chin support member 3, however, remains attached to harness 2 by strut 5 and springs 22.

Because chin support member 3 and rear head support members 4 provide such extensive support to the head, it is necessary to back one of the supports away from the wearer's head to permit removal of cervical brace 1. As can be appreciated, the movable assembly comprising chin support member 3, brace member 6 and middle member 9 permits ease of removal without affecting any adjustments. Middle member 9 can easily be swung back into place along arc 46, and with a slight force against the biasing force of springs 22 be reseated in clips 20.

Figure 3:
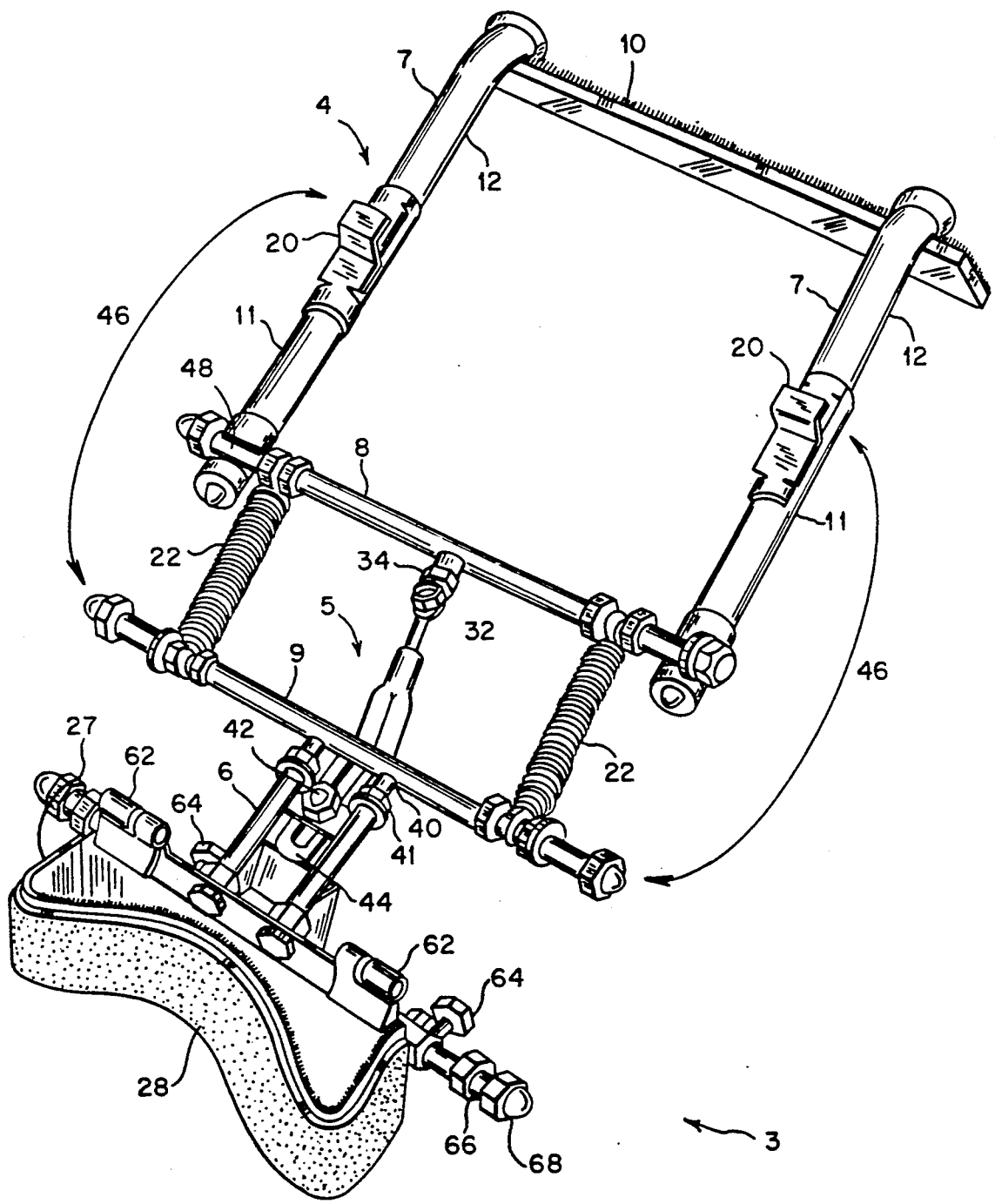
FIG. 3 is a perspective view of the chin support member in the open position.
Figure 4:
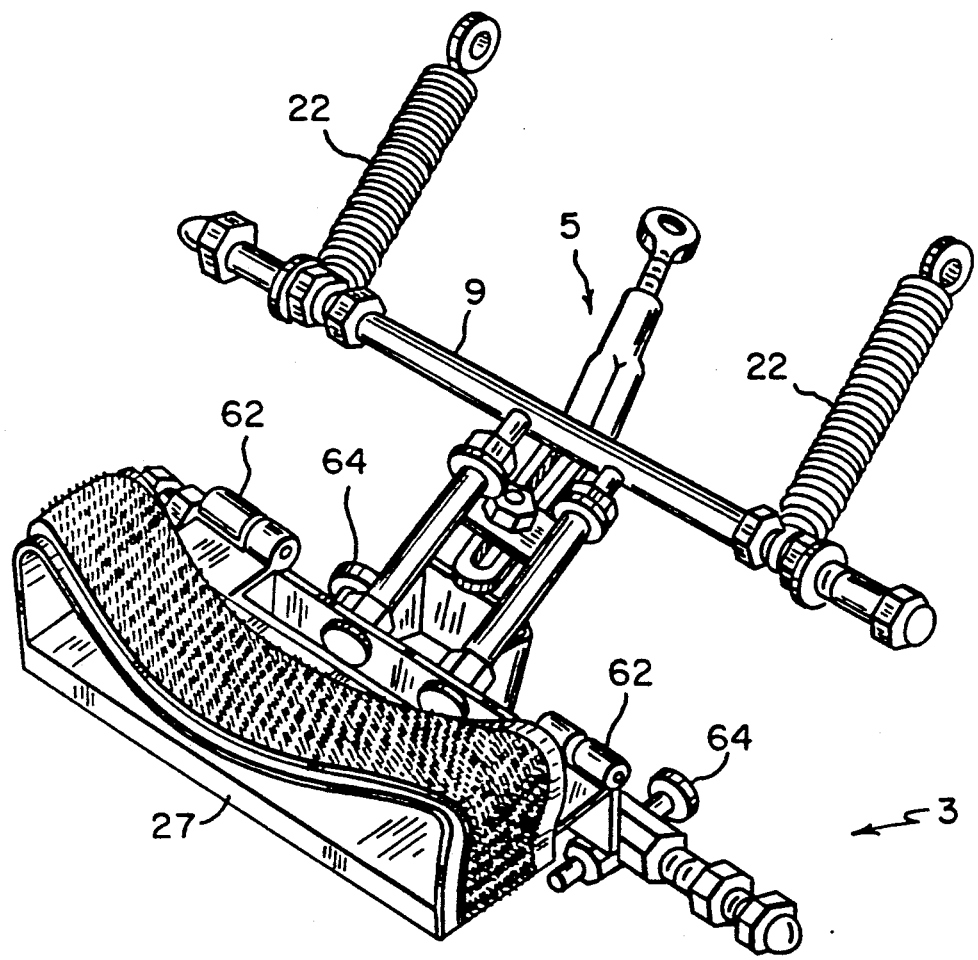
FIG. 4 is another perspective view of the chin support member.

FIG. 3 also reveals the end of guide 44 which defines the length of travel of guide screw 42. Also, a pair of hinges 62 are shown which allow for fine adjustment of arcuate member 27. Chin adjusting screws 64, as seen in FIG. 2, cause movement of arcuate member 27 constrained by hinges 62. Arcuate member 27 is shown in a partially open position in FIG. 4.

As can be appreciated, the three part adjustment of chin support member 3 allows it to be adjusted through a wide two-dimensional range. It is believed that such adjustability will accommodate a large number of wearers.

Figure 5B:
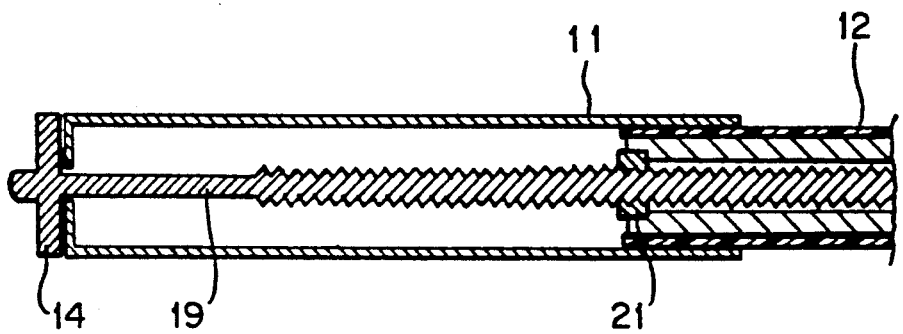
FIG. 5b is a cross-sectional view of metal tubular section 11 and plastic tubular section 12.
Figure 5A:
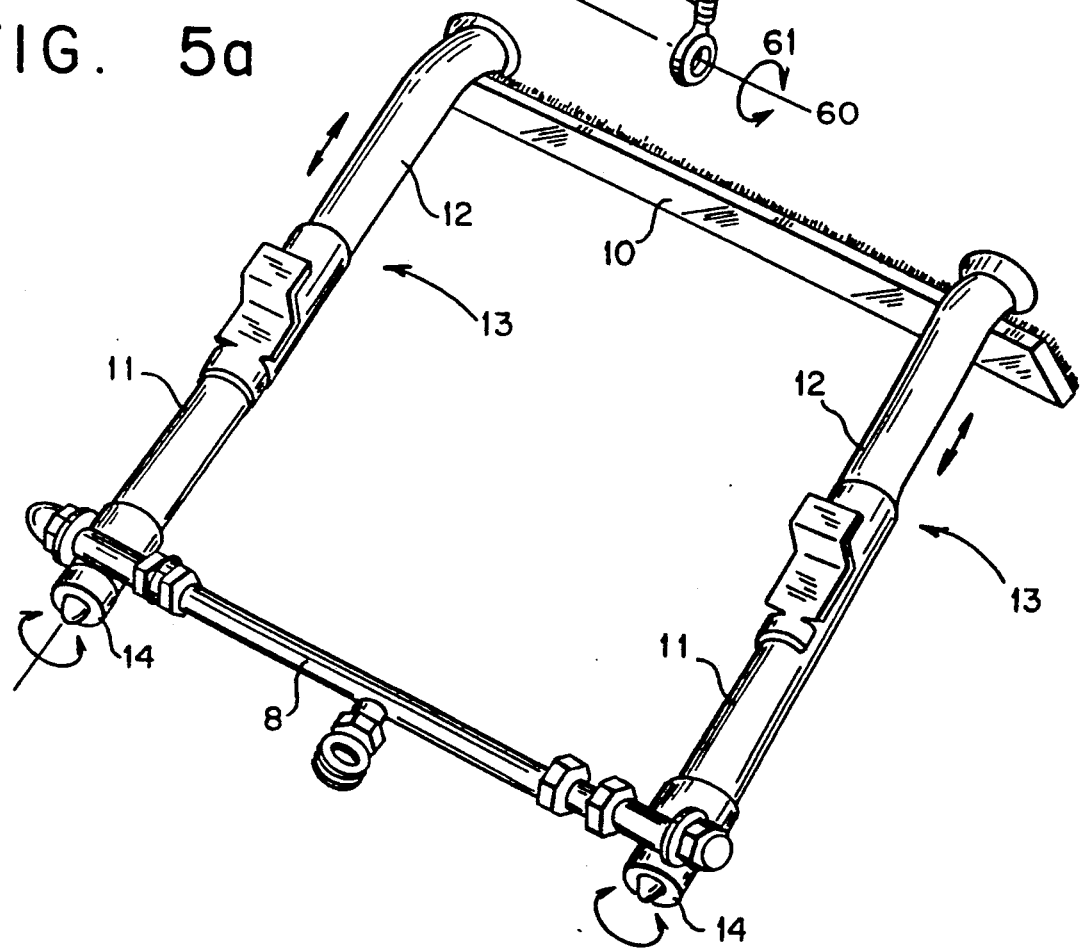
FIG. 5a is a perspective view of the torso engaging member.

As shown in FIG. 5b, metal tubular section 11 is a thin-walled hollow tube. The interior diameter of metal tubular section 11 being slightly larger than the outside diameter of plastic tubular section 12. As a result, plastic tubular section 12 extends partially into metal tubular section 11. Adjustment is provided by adjusting screws 14, which are attached to the end of bolt 19 (as shown in FIG. 5a and 5b). The end of plastic tubular section 12 is equipped with a nut 21. As adjusting screws 14 are turned clockwise, for example, it draws nut 21 and, as a result, plastic tubular member 12 toward adjusting screw 14. This shortens the distance between front member 8 and rear member 10, (also middle member 9, not shown for reasons of clarity, and rear member 10). The distance between front member 8 and middle member 9 is unchanged by this adjustment. Such adjustment allows for differences in neck and shoulder sizes of the wearers.

Figure 6:
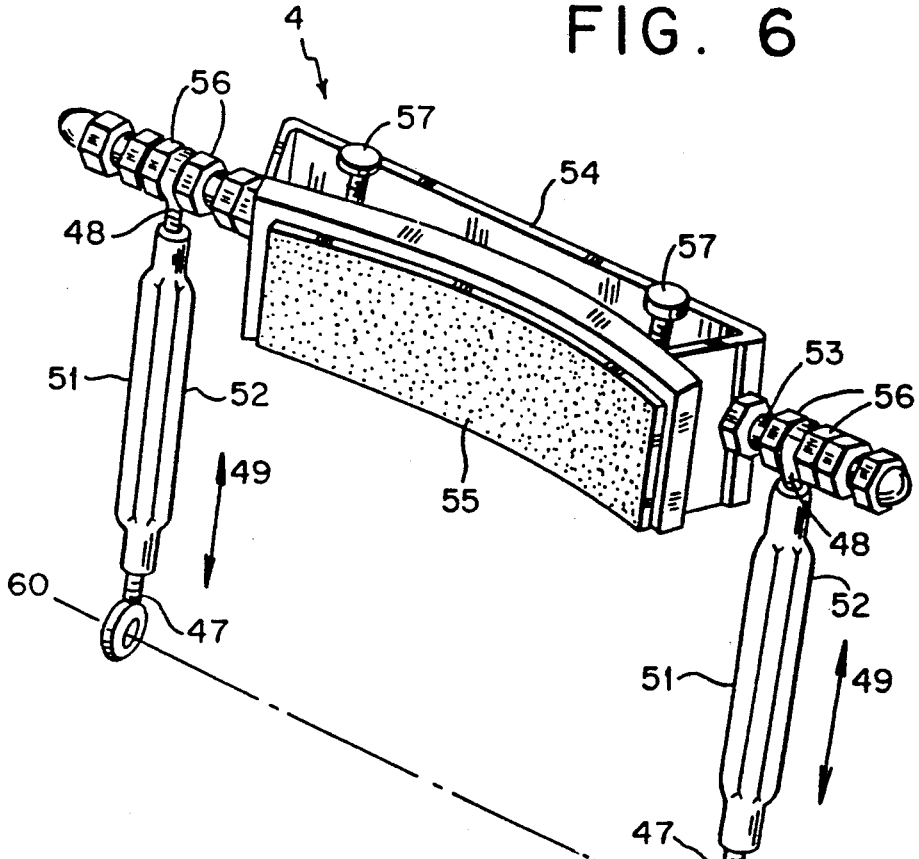
FIG. 6 is a perspective view of the head support member.

FIG. 6 shows head support member 4 with its various means of adjustment. Upstanding members 51 are ideally turnbuckles, comprised of a pair of central portions 52, and a pair of first eyelets 47, and a pair of second eyelets 48. First eyelets 47 are fixably attached to side members 7 with nuts 58 and bolts 59 (as shown in FIG. 1). Second eyelets 48 are fixably attached to threaded cross-bar 53 with nuts 56. Also attached to threaded cross-bar 53 is arcuate member 54. Conveniently located within the frame of arcuate member 54 are a pair of locking screws 57. Head support member 4 has three means for adjustment.

First eyelets 47 are fixably mounted to side members 7 in such an orientation that head support member can pivot about an axis 60—60 as shown by an arc 61. This generally brings arcuate member 54 closer or farther away from the occiput of the wearer.

Second, upstanding members 51, shown substantially in their fully collapsed position, can be expanded in a direction 49 by rotating central portion 52. For example, central portion 52 can be rotated in a clockwise direction, causing both first eyelets 47 and second eyelets 48 to unscrew due to oppositely threaded ends of central portion 52. Central portion 52 can then be rotated counter-clockwise to return upstanding members 51 to a collapsed position, for example. This adjustment generally brings arcuate member 54 upwardly or downwardly with respect to the wearer's occiput. Third, locking screws 57 can be loosened, allowing arcuate member 54 to rotate around threaded cross-bar 53. This generally allows padded surface 55 to be finely adjusted to rest flush against the rear portion of the wearer's head.

As can be appreciated the three part adjustment of head support member 4 allows it to be adjusted through a wide two-dimensional range. It is believed that such adjustability will accommodate a large number of wearers.

Figure 7:
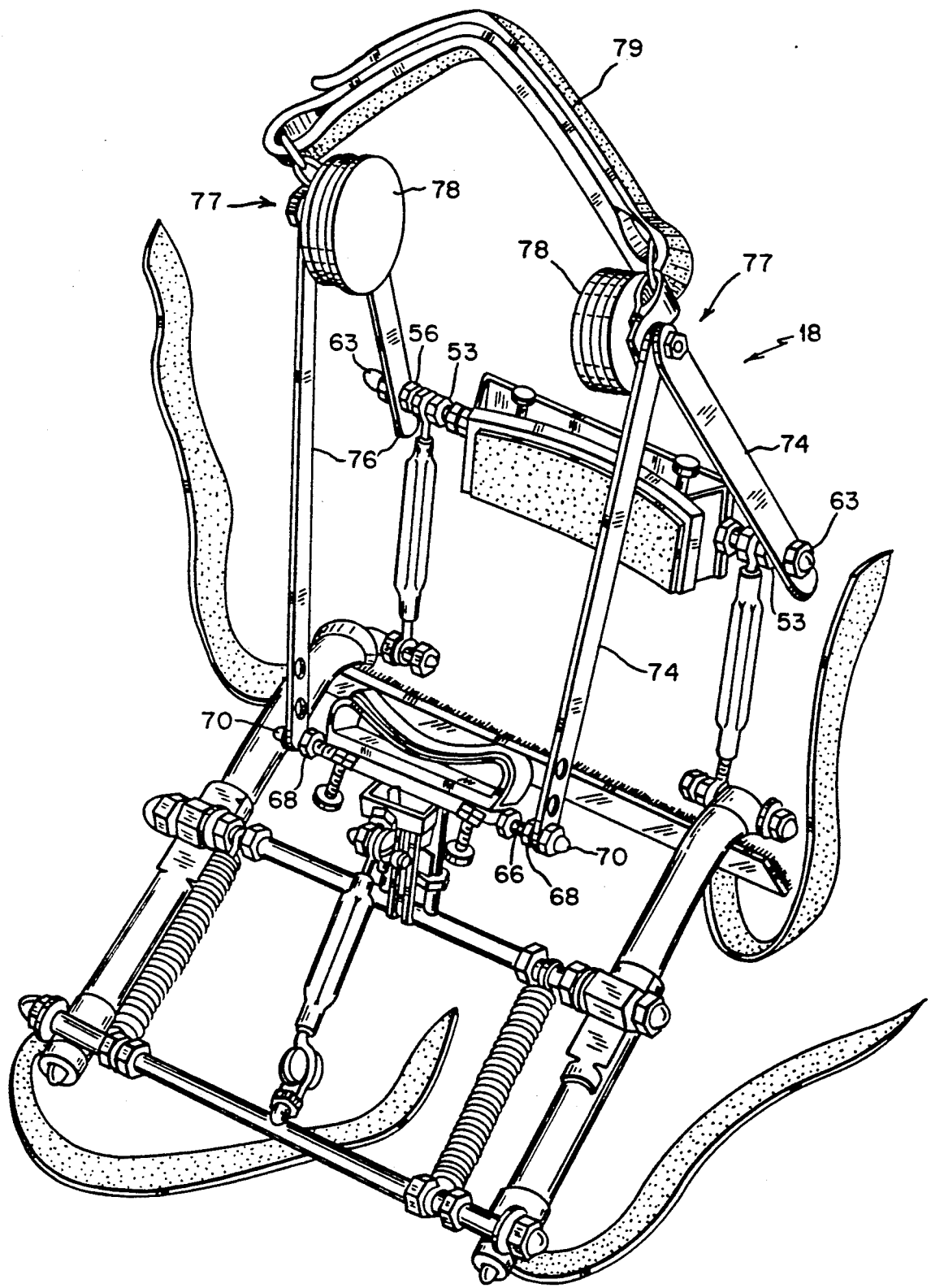
FIG. 7 is a perspective view of the cervical brace fitted with head supporting uprights.

FIG. 7 shows cervical brace 1 with a headstrap, generally denoted by numeral 18. A pair of left supporting uprights 74 are fixably attached to the left side of front headstrap bolt 66, with front headstrap nut 68 and front headstrap end nut 70, and the left side of threaded cross-bar 53, with nut 56 and a end nut 63. A pair of right supporting uprights 76 are similarly attached to the right side of front headstrap bolt 66 and the right side of threaded cross-bar 53. Left supporting uprights 74 and right supporting uprights 76 form two support points 77. On the inside of support points 77, facing the wearer's head, are located cushions 78. Also connected between support points 77 is an adjustable headstrap 79. Adjustable headstrap 79, for example, can be a multiple layered strap which fits snugly over the wearer's head to further restrict movement of the head and neck While only a single embodiment of the present invention has been shown and described, it is obvious that many changes and modifications may be made thereto without departing from the spirit and scope of the invention.

What is claimed is:

1. A cervical brace comprising:
   a torso engaging member having a back portion and a front portion, the front portion, in use, being adjacent to the front of the torso and the back portion, in use, being adjacent to the back of the torso;
   a chin support member for engaging and supporting the chin of the wearer;
   mounting means for adjustably mounting the chin support member to the torso engaging member, the mounting means including a strut and a brace member each supporting the chin support member, said strut having one end operatively coupled with the chin supporting member, and an opposite end being pivotally connected to the front portion of the torso engaging member so that the chin support member is movable backwardly and forwardly relative to the torso engaging member for accommodating, in use, different positions of a wearer's chin, said brace member operatively coupled at one end to the chin support member, and engaging at the other end a front portion of the torso engaging member at a position spaced rearwardly from the pivotal mounting of the strut, adjusting means being provided on the brace member for adjusting the length thereof, said mounting means allowing adjustment backwardly, forwardly, upwardly and downwardly, said mounting means including release means for permitting release and remounting of said brace member from the front of said torso engaging member, when released said chin support member and said brace member, secured by said strut, pivot away from the wearer's head, thereby allowing the wearer's head to be inserted and removed from the torso engaging member without affecting said adjusting means;
   a head support member for engaging and supporting the occiput of the wearer; and
   mounting means for adjustably mounting the head support member to the torso engaging member, the mounting means comprising at least one strut, said strut having one end operatively coupled with said head support member, and an opposite end movably attached to said back portion of the torso engaging member so that said head support member is movable upwardly and downwardly relative to the torso engaging member for accommodating, in use, different positions of a wearer's head, said mounting means allowing adjustment backwardly, forwardly, upwardly and downwardly, so that said chin support member and said head support member cooperatively restrict movement of the wearer's head.

2. A cervical brace according to claim 1, wherein said adjusting means provided on said brace member comprises a pair of adjusting screws and nuts mounted on said brace member.

3. A cervical brace according to claim 2, wherein said adjusting means provided on said brace member and said strut form a three-point support structure for said chin support member, said adjusting means being removable and interchangeable with adjusting means of varying lengths for accommodating the length of the wearer's neck.

4. A cervical brace according to claim 1, wherein said strut of said chin support member is a turnbuckle.

5. A cervical brace according to claim 1, wherein said mounting means for mounting said head support member includes a pair of struts.

6. A cervical brace according to claim 5, wherein said struts for said head support member are turnbuckles and are removable, thereby allowing the wearer's head to be inserted and removed through the back portion of said torso engaging member.

7. A cervical brace according to claim 1, wherein said mounting means for said chin support member has an upper portion which is pivotally mounted about an axis located between said chin support member and the wearer and adjustable by adjusting screws.

8. A cervical brace according to claim 1, wherein said chin support member comprises a transverse member of arcuate shape for engaging beneath the chin.

9. A cervical brace according to claim 1, wherein said head support member comprises a transverse member of arcuate shape for engaging behind the wearer's head.

10. A cervical brace according to claim 1, wherein said torso engaging member comprises:
    a pair of side members which support said head support member and its mounting means, the distance between said side members being adjustable as well as the contour of said side members for accommodating the shape of the wearer's shoulders;
    a front member extending between said pair of side members;
    a middle member extending between said pair of side members, said front an middle member being positioned adjacent to the front of the torso and supporting said chin support member and its mounting means; and
    four removable head supporting uprights each with a top end and a bottom end extending upwardly from said chin support member and said head support member to, in use, extend adjacent the sides of the wearer's head, said uprights being releasably engageable with said chin support member and said head support member.

11. A cervical brace according to claim 10, wherein said strut supporting said chin support member is pivotally connected to said front member.

12. A cervical brace according to claim 10, wherein said brace member supporting said chin support member is pivotally connected to said middle member.

13. A cervical brace according to claim 12, additionally including spring means and a pair of clips located on said side members, said middle member being releasably mounted to said side members by spring means attached to said middle member and said front member for biasing said middle member toward said front member against said clips.

14. A cervical brace according to claim 13, wherein said chin support member, said brace member and said middle member are releasably mounted to said side members.

15. A cervical brace according to claim 14, wherein said chin support member, said brace member and said middle member are releasably mounted and pivot away from the wearer's head secured by said strut, which is pivotally connected to said front member, thereby allowing the wearer's head to be inserted and removed from the torso engaging member.

16. A cervical brace according to claim 15, wherein said chin support member, said brace member and said middle member can be released and re-mounted without affecting said adjusting means.

17. A cervical brace according to claim 10, wherein two of said head supporting uprights are attached at their bottom ends respectively to the left end of said chin supporting member and said head support member and two of said head supporting uprights are attached at their bottom ends respectively to the right end of said chin supporting member and said head support member, the width between the bottom attached ends being adjustable to accommodate the width of the wearer's head.

18. A cervical brace according to claim 17, wherein the top ends of the two left head support uprights are attached to each other forming a left support point and the top ends of the two right head support uprights are attached to each other forming a right support point.

19. A cervical brace according to claim 18, wherein a variable length strap extends from said left support point to said right support point over the top of the wearer's head thereby further restricting movement of the wearer's head.

20. A cervical brace according to claim 1, wherein said torso engaging member includes a strap extending from each end of said pair of side members, the straps attached to the left-side member, in use, releasably engaging with each other under the wearer's left armpit and the straps attached to the right-side member releasably engaging with each other under the wearer's right armpit.

21. A cervical brace according to claim 1, wherein said torso engaging member is strapless.

22. A cervical brace according to claim 1, wherein said torso engaging member has a maximum of two pairs of straps, each pair located on said harness so as to attach under the wearer's arm.

23. A cervical brace according to claim 10, wherein the distance between the middle member and the head support member is adjustable, said side members including a front section nd a rear section, said rear section fitting within said front section and including an interior shaft which extends the entire length of said rear section, said front section including an interior threaded rod, said shaft configured and designed to ride along said rod when rotated for lengthening or shortening said side members.

* * * * *